United States Patent [19]

Lewis et al.

[11] Patent Number: 5,151,369
[45] Date of Patent: Sep. 29, 1992

[54] LITHIUM SALTS AS RED BLOOD CELL LYSING AND HEMOGLOBIN DENATURING REAGENTS

[75] Inventors: Lynette A. Lewis, Goshen; M. Teresa Yip, Elkhart, both of Ind.

[73] Assignee: Miles Inc., Elkhart, Ind.

[21] Appl. No.: 522,835

[22] Filed: May 14, 1990

Related U.S. Application Data

[63] Continuation-in-part of Ser. No. 379,582, Jul. 13, 1989, abandoned.

[51] Int. Cl.⁵ .................... G01N 33/72; G01N 33/50
[52] U.S. Cl. ........................................ 436/67; 436/66; 436/17
[58] Field of Search ............ 436/66, 67, 17, 501, 436/521, 808; 422/68, 55

[56] References Cited

U.S. PATENT DOCUMENTS

| | | | |
|---|---|---|---|
| 4,255,385 | 3/1981 | Stroupe et al. | 436/67 |
| 4,582,789 | 4/1986 | Sheldon, III et al. | 435/6 |
| 4,801,299 | 1/1989 | Brendel et al. | 435/1 |
| 4,853,338 | 9/1989 | Benerra et al. | 436/66 |
| 4,880,749 | 11/1989 | Burdick et al. | 422/57 |

FOREIGN PATENT DOCUMENTS

| | | |
|---|---|---|
| 0164960 | 12/1985 | European Pat. Off. |
| 0315864 | 5/1989 | European Pat. Off. |
| 0315866 | 5/1989 | European Pat. Off. |
| 0407860 | 1/1991 | European Pat. Off. |

OTHER PUBLICATIONS

Darnell, James; Lodish, Harvey; Baltimore, David; "Molecular Cell Biology" pp. 167–169, FIG. 5–41.
Harrington, Comp. Biochem. Physiol. 76B:235–240 (1983).
Pesce and Giacomo, Ann. Clin. Lab. Sci. 18:168–163 (1988).

*Primary Examiner*—David L. Lacey
*Assistant Examiner*—Thomas E. Daley

[57] ABSTRACT

Use of a lithium salt, particularly lithium thiocyanate, as an agent for lysing red blood cells and denaturing hemoglobin in the performance of an immunoassay to detect the relative amount of a hemoglobin derivative in a blood sample. The method is particularly useful in the determination of hemoglobin A1c. The method rapidly releases hemoglobin from red blood cells by lysis and exposes the epitope that is characteristic of the A1c form. Low concentrations of the lithium salt provide rapid release and denaturation of hemoglobin without the need for dilution prior to the performance of the immunoassay.

6 Claims, 6 Drawing Sheets

LITHIUM SALTS AS RED BLOOD CELL LYSING AND HEMOGLOBIN DENATURING REAGENTS

CROSS-REFERENCE TO RELATED APPLICATION

This application is a continuation-in-part of application Ser. No. 379,582, filed Jul. 13, 1989, abandoned Nov. 4, 1991.

BACKGROUND OF THE INVENTION

The present invention relates to methods and reagents for the lysis of erythrocytes in a blood sample. More particularly, the invention relates to the release of hemoglobin by lysis of erythrocytes and the denaturation thereof for the purpose of immunoassay determination of a particular hemoglobin derivative such as hemoglobin A1c.

The determination of the relative amount of hemoglobin that exists in the bloodstream in a particular derivative form generated by in vivo processes is of considerable importance to medical diagnosis. Of particular significance is the measurement of glycated hemoglobins to assess the long term blood glucose control in diabetes mellitus. The glycated form of hemoglobin that perhaps is the most important in diabetes management is the derivative commonly known as hemoglobin A1c. This hemoglobin derivative is produced in vivo by the nonenzymatic reaction of glucose with the hemoglobin protein. Glucose becomes covalently attached in a rearranged form to the amino-terminal valine residue of the beta-chain in native hemoglobin. Normal individuals have between about 3 and about 6 percent of their total hemoglobin in the A1c form, while an uncontrolled diabetic individual could have as much as 3 to 4-fold higher levels of this hemoglobin derivative in the bloodstream.

A variety of methods have been developed for the measurement of glycated hemoglobin. The conventionally used methods are based on diverse techniques such as cation exchange chromatography, electrophoresis, and dye complexation (hydroxyfurfural/thiobarbituric acid). These techniques are well known to be tedious, complex, requiring special technical skills, and suffer from imprecision and nonspecificity. Quite recently, monoclonal antibodies specific for the the glycated N-terminal peptide residue that characterizes hemoglobin A1c have been developed, enabling the detection of this hemoglobin derivative by convenient immunoassay approaches (see U.S. Pat. No. 4,647,654).

The immunoassay determination of hemoglobin A1c using monoclonal antibodies is highly specific and the procedure used is significantly less tedious and complex than the conventional prior art methods. Nevertheless, the optimal hemoglobin A1c immunoassays have been found to require the denaturation of hemoglobin in order to expose the glycated N-terminal peptide epitope for antibody binding (see U.S. Pat. No. 4,658,022). Conditions which have been shown to provide the necessary degree of denaturation of hemoglobin for exposure of the A1c epitope have typically also be sufficient for denaturation of antibody reagents used in the immunoassay detection of the exposed epitope. For example, when using chemical denaturants, it has generally been found necessary to dilute the denatured hemoglobin mixture sufficiently to reduce the concentration of denaturant below that which would significantly interfere with the immunoassay reaction. Such a dilution step is inconvenient and can introduce error to the assay measurement.

An improved denaturant reagent for use in the immunoassay determination of hemoglobin derivatives such as hemoglobin A1c is described in European patent publication 315,864. The blood sample is treated with the combination of a thiocyanate salt and an oxidant to release and denature the hemoglobin in the sample and to convert hemoglobin to its spectrophotometrically detectable met-hemoglobin form. In this way, total hemoglobin can be determined by absorbance measurement of met-hemoglobin and the A1c portion determined and related to total hemoglobin content by immunoassay.

The presence of the met-hemoglobin oxidant during denaturation was found to significantly increase the rate of denaturation of hemoglobin, thereby reducing the overall assay time and improving the reliability of the determination. However, the concentration of thiocyanate salt required for optimal denaturation is sufficiently high that a reduced immunoassay response has been observed. Thus, a dilution step is generally required after denaturation in order to reduce the thiocyanate concentration to a level that does not significantly interfere with the ability of antibody to bind to the exposed A1c epitope.

SUMMARY OF THE INVENTION

It has been unexpectedly found that the nature of the counter cation in the denaturant salt, particularly when the denaturant salt is a thiocyanate salt, has a significant effect on its ability to denature hemoglobin for purposes of detecting hemoglobin derivatives such as hemoglobin A1c by immunoassay. It has been found that the use of a lithium salt form of an anion capable of lysing erythrocytes and of denaturing released hemoglobin (including the derivative forms thereof present in a test sample) significantly increases the rate of lysis and denaturation without interfering significantly with the immunoassay. Significantly, the use of lithium denaturant salts of the present invention has been found to eliminate the need for dilution of the denatured hemoglobin mixture prior to performance of the immunoassay. The lithium salt forms of lysing/denaturing anions, such as thiocyanate, have been found to be effective to rapidly lyse erythrocytes and denature released hemoglobin at concentrations low enough that the immunoassay reaction can take place without significant interference directly in the resulting denatured mixture.

Accordingly, the lithium salts of the present invention are useful as lysing/denaturing reagents in analytical methods for determining a particular hemoglobin derivative in a blood sample. In such methods, the blood sample is treated with the lysing/denaturing reagent to lyse erythrocytes and to denature a detectable amount of the hemoglobin derivative of interest that is released from the erythrocytes, and the resulting mixture is assayed by immunoassay to detect the denatured form of the hemoglobin derivative therein. Normally, it will be desired to relate the amount of the hemoglobin derivative of interest as a fraction or percentage of the total amount of hemoglobin in the sample. In such case, the blood sample is additionally treated with an oxidant, such as a ferricyanide salt, to convert the released hemoglobin (including all derivative forms thereof) to its met-hemoglobin form. The resulting met-hemoglobin in the mixture can then be assayed spectrophotometrically to provide a measure of the total hemoglobin content of the sample, and the percent that is in the form of the hemoglobin derivative of interest can be calculated from the spectrophotometric met-hemoglobin and hemoglobin derivative immunoassay results.

In the course of discovering the improved properties of the lithium salt forms of lysing/denaturing anions, it was also found that the particular salts lithium thiocyanate and lithium perchlorate are superior to other cation forms in the lysis of erythrocytes irrespective of denaturation. Such property of these lithium salts is useful in methods, including analytical methods, requiring the lysis of erythrocytes such as to release a substance to be detected, to remove interferences, and the like.

DESCRIPTION OF THE PREFERRED EMBODIMENTS

Figure 1:
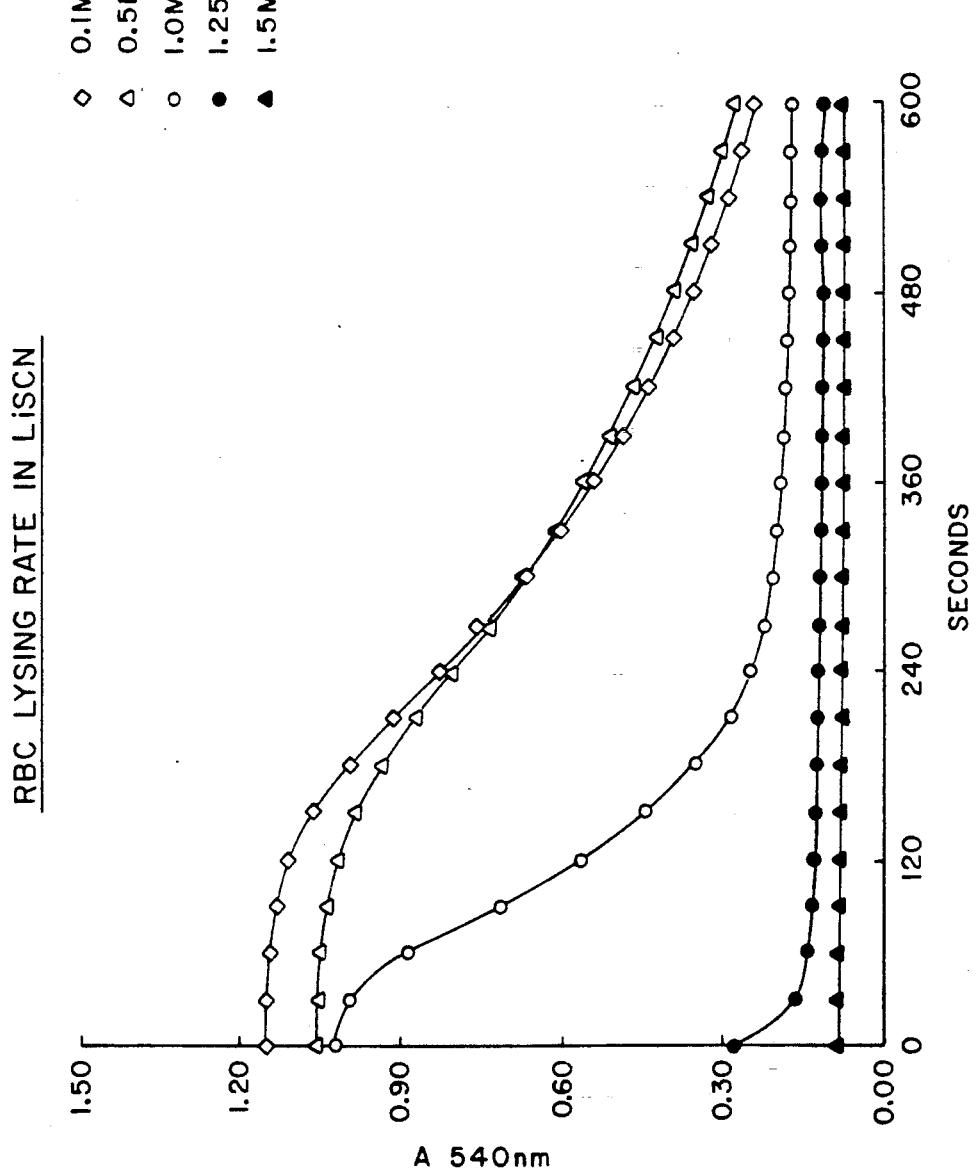
FIGS. 1-4 are graphs showing the time courses for the lysis of red blood cells (RBC) using various thiocyanate salts. The data demonstrates that the lithium salt is the most efficient for RBC lysis.
Figure 2:
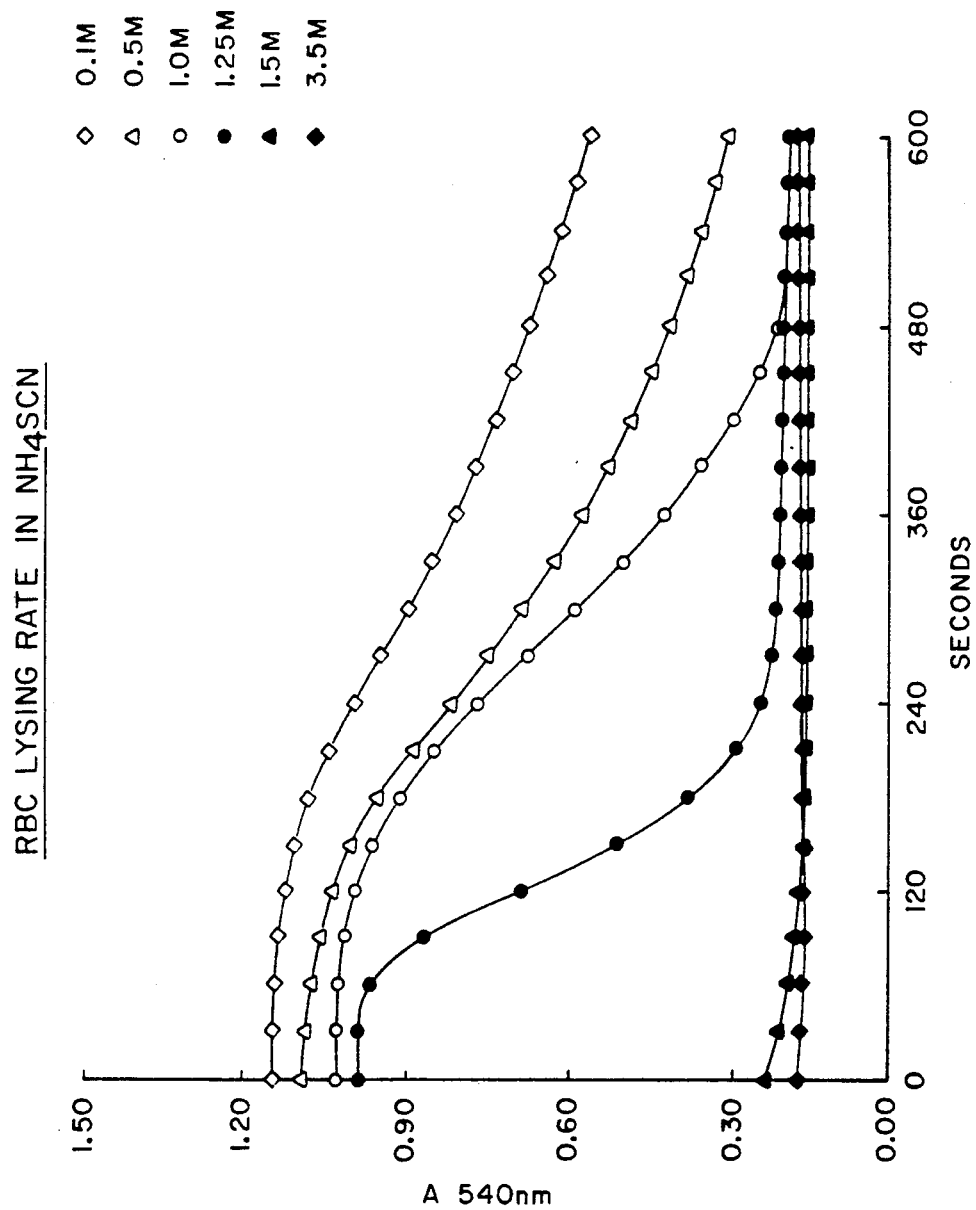
Figure 3:
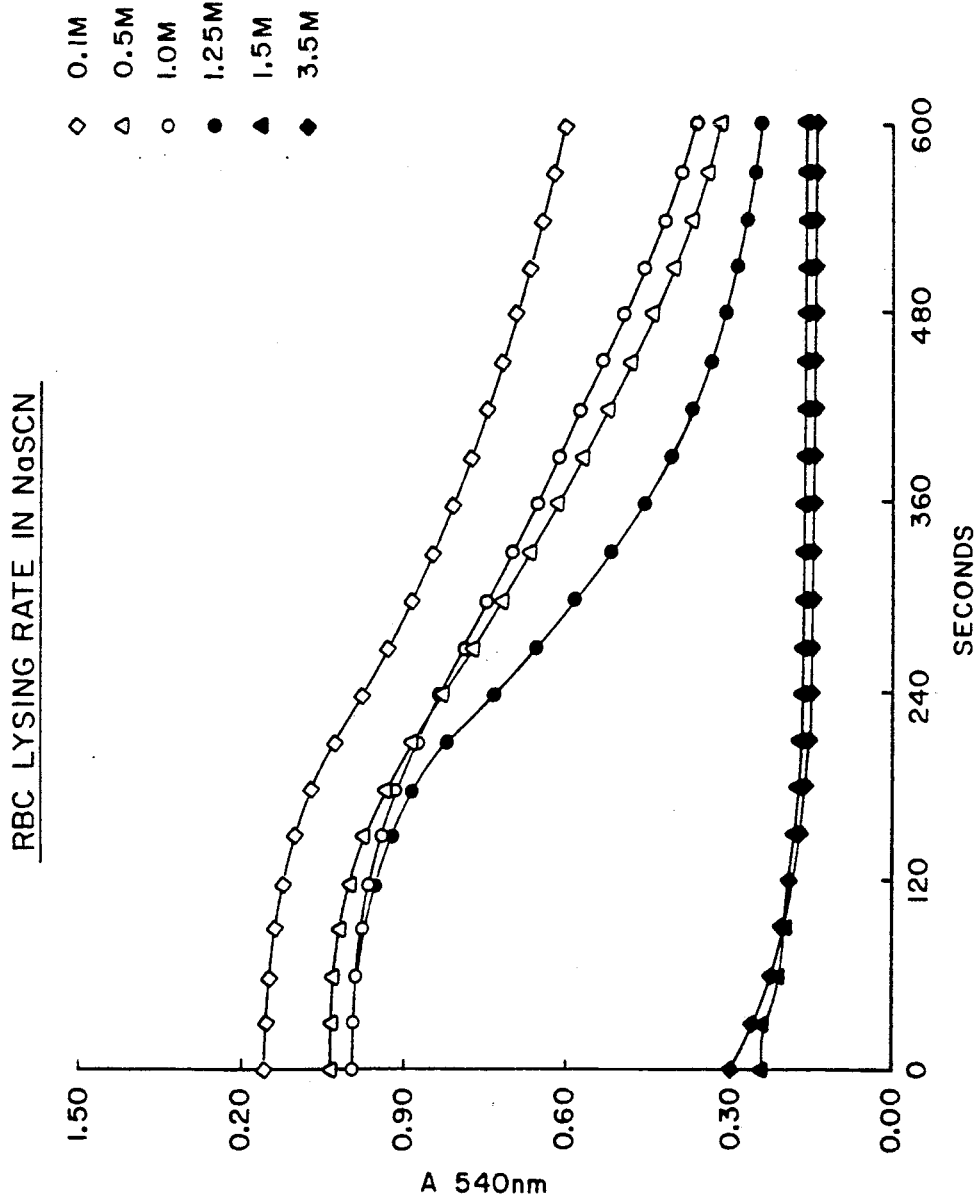
Figure 4:
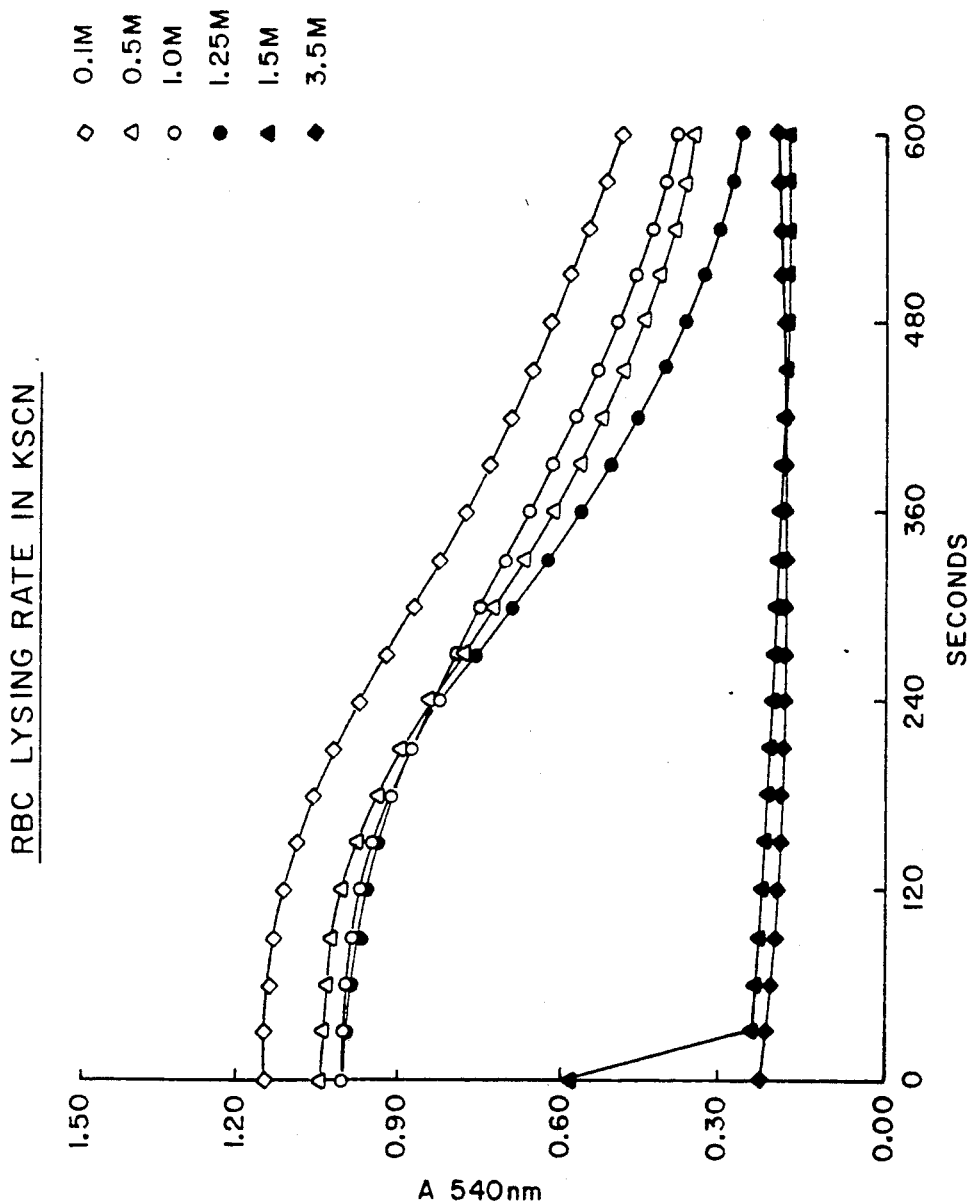

The present invention involves the use of a lithium salt form of an anion which will be referred to herein as a lysing/denaturing anion. The lysing/denaturing anion can be selected from any which are known or found to be effective to lyse erythrocytes to release hemoglobin therefrom and to denature the hemoglobin derivative of interest sufficiently for detection by immunoassay. The most preferred anion is thiocyanate. Other anions which can be used include, without limitation, perchlorate, cyanide, iodate, and periodate. Other functional anions will be recognized by those working in the field or will be readily determinable by routine experimentation.

The preferred lysing/denaturing reagent therefore is lithium thiocyanate. In general, concentrations of lithium thiocyanate above about 0.5 molar (M) in the medium or mixture in which the hemoglobin derivative of interest is to be released and denatured will be effective at temperatures between about room temperature (i.e., around 20°-25° C.) and slightly elevated temperatures (e.g., up to about 37° C.) and in the presence of oxidant (described in detail below). Maximum efficiency of lysis and denaturation occurs at about 1.25M, although concentrations up to about 3.5M have been found to be tolerable by the immunoassay without dilution. However, in order to operate at concentrations above about 3.0M, it can be necessary to make modifications of the immunoassay reagents or assay protocol which are economically impractical or undesirable, e.g., increasing the concentration of reagent antibody. Higher concentrations, e.g., up to 6M, can be used for lysis, however, the resulting mixture will normally require dilution to below 3.5M for the immunoassay step. Therefore, the concentration of lithium thiocyanate in the lysis/denaturation medium will usually be from about 0.5 to about 3.5M, and more preferably below about 3.0M. A more preferred range of concentration is between about 1.0 and about 2.0M, with 1.25M being presently considered optimal and most preferred.

The above concentration ranges will vary somewhat with temperature and with the concentration of oxidant. One skilled in the art will be able to optimize the lysis/denaturing conditions for a particular hemoglobin derivative immunoassay. Concentration ranges for the lysis/denaturing reagent, the effect of oxidant, the effect of temperature, and the like can be readily determined empirically for any particular assay. Presently, the most preferred conditions are 1.25M lithium thiocyanate, with 0.76 mM ferricyanide as oxidant, at 37° C.

The determination of the concentration or amount of a particular hemoglobin derivative in a blood sample can be performed in the absence of oxidant. Oxidant serves to enhance the denaturation effects of thiocyanate as a lysing/denaturing anion, and also to convert hemoglobin to met-hemoglobin to provide a means for total hemoglobin measurement. If desired, one can determine the absolute concentration or amount of the hemoglobin derivative (without regard for the concentration or amount of total hemoglobin in the sample) by immunoassay, or can perform a separate total hemoglobin assay on a second sample and correlate the results with the hemoglobin derivative immunoassay in order to calculate percent or proportion of hemoglobin in the derivative form.

It is particularly advantageous to perform a determination of the relative amount of the hemoglobin derivative in a single sample of blood. The combined use of a lithium thiocyanate lysis/denaturing reagent with oxidant provides a means of rapidly and reproducibly converting essentially all of the hemoglobin in the blood sample into a denatured thiocyan-met-hemoglobin form. This form of hemoglobin serves as the basis for measuring total sample hemoglobin, with the denatured form of the particular hemoglobin derivative of interest serving as the analyte in the immunoassay. As described below, the immunoassay is preferably based on the specific affinity of a monoclonal antibody for the denatured form of the hemoglobin derivative of interest.

When used, the oxidant can be selected from essentially any inorganic or organic oxidizing agent of sufficient electrochemical potential to convert the native hemoglobin ferrous ion to its ferric met-hemoglobin form. Of course, an oxidant candidate selected by its oxidation potential will be tested in the assay system to assure that it will not interfere significantly with the total and hemoglobin derivative assays. A variety of oxidants are known in the literature to be effective in converting hemoglobin to its met-hemoglobin form [see Advances in Clinical Chemistry 8:142-185 (1965)]. Oxidants that qualify based on oxidation potential include ferricyanide, iodate, chlorate, bromate, chromate, mercuric chloride, ceric and thallium ions, hypochlorite, periodate, iodide, hydroxyamine, bromosuccimide, chlorosuccimide, chloroamine, perchlorate and peroxide. The degree of enhancement of the denaturation kinetics, yielding reduced time for the required denaturation, will of course vary according to the oxidant used. Empirical testing can be readily performed to enable selection of an oxidant that, in combination with lithium thiocyanate, provides sufficiently rapid denaturation.

Sufficient denaturation shall be understood in the present context to mean the point at which the denaturation of hemoglobin in the blood sample provides substantially the maximum amount of the denatured form of the hemoglobin derivative of interest that can be detected using the selected immunoassay. Therefore, sufficient denaturation does not intend necessarily the complete disruption of all tertiary and secondary structure of the hemoglobin protein, but rather maximum exposure of the epitope of the hemoglobin derivative detected by the selected immunoassay means. Normally, the immunoassay is based on monoclonal antibody specificity for a unique epitope that characterizes the hemoglobin derivative.

The oxidant will be added in excess amounts, for example, in 5-fold excess of the amount of heme normally present in the sample. Amounts up to 20-fold excess can be used advantageously. Appropriate amounts for particular assays can be determined by the worker in the field.

The thiocyanate/oxidant denaturant pair can be mixed with the blood sample stepwise or, as would be preferred, simultaneously. Normally, a denaturant reagent solution of the thiocyanate and oxidant is prepared and mixed directly with the blood sample. For reasons of stability, the denaturant reagent solution will oftentimes be prepared only immediately prior to its use in the assay. However, where stability will allow or where stabilizing agents or construction of the device are used which permit the thiocyanate salt and oxidant to be together, the denaturant reagent solution can be stored and/or packaged over prolonged time periods. The denaturant components can be in a dry form and mixed or otherwise associated so as to form the reagent solution upon rehydration with test sample and/or a diluent or buffer.

It is contemplated that the present method applies to the assay of any hemoglobin derivative in blood which is detected in its denatured form by immunoassay. Such hemoglobin derivatives, include without limitation, acetaldehyde-hemoglobin adducts associated with alcohol abuse, urea-hemoglobin adducts present in the blood of uremic patients, aspirin-hemoglobin complexes, and particularly the family of glycated hemoglobins formed by nonenzymatic reaction of glucose with reactive amine groups on the hemoglobin protein. The present invention is especially applicable to the determination of hemoglobin A1c as defined above.

Where it is desired to determine the relative amount of the hemoglobin derivative in a blood sample, the treated, denatured blood sample is separately assayed for total met-hemoglobin and for the hemoglobin derivative of interest, followed by a mathematical correlation of the results to give a measure of the relative amount of the blood hemoglobin that is in the derivatized form of interest. Total met-hemoglobin can be measured in any conventional manner such as the Drabkins' procedure (National Commission for Clinical Laboratory Standards of the U.S., Proposed Standard PSH-15). A most convenient method for measuring total met-hemoglobin is by measuring its absorbance in solution at a characteristic wavelength, e.g., 540 nm.

The determination of the hemoglobin derivative will normally be performed by immunoassay. As described in the aforementioned U.S. Pat. Nos. 4,647,654 and 4,658,022, monoclonal antibodies can be developed which bind specifically to the epitope that characterizes the hemoglobin derivative, e.g., hemoglobin A1c, in the denatured protein. The particular immunoassay technique and format, as well as the labeling approach and detection signal generated, is not critical to the present invention. In principle, nonradioisotopic methods are preferred, such as those based on the use of enzyme labels (ELISA) and the like.

A method that is particularly useful because it can be performed without a separation step and provides a measurable absorbance change related to analyte concentration is particle agglutination inhibition immunoassay. Such an assay is based on the specific interaction of an antibody particle reagent and an agglutinator reagent. The antibody particle reagent comprises the antibody, or a fragment thereof, bound to a water suspendable particle (e.g., a polystyrene or other latex). The agglutinator comprises a plurality of epitopic binding sites for the antibody reagent. In the absence of analyte, the antibody particle and agglutinator bind to one another to form a light scattering complex that is readily quantitated by turbidimetric measurement. In the presence of increasing amounts of analyte, the turbidity of the solution decreases as antibody particles become bound to the analyte and cannot bind to the agglutinator. The agglutinator can conveniently comprise a polymer backbone to which are attached a number of organic moieties, e.g., peptide residues, which define the epitope that characterizes the hemoglobin derivative of interest. For example, for hemoglobin A1c determinations, the epitopes can comprise glycated peptide residues of a few amino acid units corresponding to the sequence of the glycated N-terminal residue in hemoglobin A1c.

The respective total met-hemoglobin and derivative hemoglobin assays can be performed on the same of different portions of the treated blood sample. In the latter case, a first volume of the treated sample is directly assayed for met-hemoglobin, usually after making an appropriate dilution in buffer, and a second volume is assayed for the denatured hemoglobin derivative as described above. It is also possible to conduct both assays in series on the same treated sample volume such as by making an appropriate dilution of the treated sample, assaying for thiocyan-met-hemoglobin, and then either adding the reagents of the immunoassay system or adding the solution to such reagents.

The present invention also provides a test system for determining the hemoglobin derivative of interest in a blood sample. The test system will comprise the lysing-/denaturant reagent of the present invention and reagents for immunoassaying a lysed and denatured blood sample for the amount of the denatured form of the hemoglobin derivative released from erythrocytes by the action of the lysing/denaturing reagent on the sample. Where the assay is intended to provide a determination of the relative amount of hemoglobin that is in the derivative form of interest, the test system will preferably comprise in addition an oxidant as described above.

The test system can be in a variety of forms, from a test kit comprising individual containers holding the various reagent components to a unitized test device containing all of the necessary test reagents and which is manipulable to perform all of the assay steps within the singular device (an example of the latter is described in commonly assigned, copending U.S. patent application Ser. No. 179,843, filed Apr. 11, 1988, now U.S. Pat. No. 4,990,075 and entitled "Reaction Vessel for Performing Sequential Analytical Assays".

As stated previously, in the course of discovering the improved properties of the present lithium salts as lysing/denaturing reagents in hemoglobin derivative assays, it was also found that certain lithium salts have improved erythrocyte lysing properties irrespective of denaturation of released hemoglobin. As compared with the corresponding sodium, potassium, or ammonium salts, the lithium salts showed an unanticipated enhanced ability to lyse erythrocytes. As demonstrated in the examples below, two particular lithium salts, lithium thiocyanate and lithium perchlorate, showed improved lysing properties compared to other cationic forms thereof. Such lithium salts will be advantageous when it is desired to lyse erythrocytes irrespective of whether or not it is further desired to denature constituents released therefrom.

As erythrocyte lysing agents, the salts lithium thiocyanate and lithium perchlorate have shown themselves to provide more rapid and complete lysis at lower concentrations than their sodium, potassium, and ammonium counterparts. On the other hand, other salts have shown little or no ability to effectively lyse erythrocytes, particularly chloride, hydroxide, and acetate salts, irrespective of the cation. It is anticipated that where the sodium, potassium, or ammonium salt of a particular anion exhibits erythrocyte lysing properties, the lithium form of such salt will exhibit enhanced lysis. Accordingly, such lithium salts are contemplated within the spirit of the present invention and will be considered equivalents to lithium thiocyanate and lithium perchlorate for the purposes hereof.

The present invention will now be illustrated, but is not intended to be limited, by the following examples.

EXAMPLES A. Lysis of Red Blood Cells (RBC) by Thiocyanate Salts

Thiocyanate solutions of 1.5M containing different cations were prepared in 200 mM glycine with 0.25% potassium ferricyanide at pH 9 and were equilibrated at 37° C. A 5 μl sample of fresh whole blood was pipetted into 2.5 ml of thiocyanate solution and the absorbance at 540 nm was measured at 37° C. and recorded at 30 second intervals for about 10 minutes. The rate of lysis in the presence of the ferricyanide oxidant was determined as the time required to reach an absorbance minimum (complete lysis). The results are shown in Table 1.

TABLE 1

| Cation | Time Required for Complete Lysis |
| --- | --- |
| Guanidine | <1 min* |
| Lithium | ~1 min |
| Ammonium | ~3 min |
| Sodium | ~5 min |
| Potassium | ~8 min |

*Guanidine is not compatible with the HbAlc immunoassay

The above experiment was repeated with thiocyanate solutions at different concentrations. Thiocyanate solutions were prepared in 200 mM glycine, pH 9, containing 0.25% potassium ferricyanide and were equilibrated at 37° C. To measure the rate of lysis, 5 μl of fresh whole blood was pipetted into 2.5 ml of thiocyanate solution. The absorbance at 540 nm was measured at 37° C. and recorded at 30 second intervals for 10 minutes. The rate of lysis was determined as the time required to reach an absorbance minimum (complete lysis). The results are shown in FIGS. 1–4 and summarized in Table 2.

TABLE 2

| Cation | Thiocyanate Concentration, M | Time Required For Complete Lysis, Min. |
| --- | --- | --- |
| potassium | 0.1 | >10 |
| | 0.5 | >10 |
| | 1.0 | >10 |
| | 1.25 | >10 |
| | 1.5 | 6 |
| | 3.5 | 1.5 |
| sodium | 0.1 | >10 |
| | 0.5 | >10 |
| | 1.0 | >10 |
| | 1.25 | >10 |
| | 1.5 | 5 |
| | 3.5 | 4 |
| ammonium | 0.1 | >10 |
| | 0.5 | >10 |
| | 1.0 | 9 |
| | 1.25 | 6 |
| | 1.5 | 4 |
| | 3.5 | <0.5 |
| lithium | 0.1 | >10 |
| | 0.5 | >10 |
| | 1.0 | 5 |
| | 1.25 | 1 |
| | 1.5 | <0.5 |

B. Lysis of RBC with Hemoglobin Denaturation Using Thiocyanate Salts

Reagents (1) Lysing/denaturing reagent: 0.5, 1.0, or 1.5M lithium thiocyanate or 1.5M ammonium thiocyanate in 200 mM glycine containing 0.25% potassium ferricyanide at pH 9.0

(2) Antibody-Latex reagent: The antibody coating is done at a latex concentration of 0.5% [0.085 μm diameter polystyrene latex, Seragen, Indianapolis, Ind., USA] and the antibody [Monoclonal antibody prepared as described in U.S. Pat. No. 4,647,654, purified from ascites fluid by protein A affinity chromatography (BioRad Laboratories, Richmond, Calif., USA)] is normally used in a final concentration of 1 mg/ml in the coating reaction.

An antibody solution at 2× concentration is prepared by diluting the required amount of antibody into a 10 mM glycine buffer with added NaCl to give the final conductivity desired (between 0.5 and 1.8 mmho). The 2% latex is diluted to 2× concentration (or 1%) by mixing with an equal volume of the 10 mM glycine buffer. The reaction is initiated by pouring the latex suspension into a vessel containing the antibody solution. The antibody solution is mixed with a magnetic stir bar when the latex is added. All solutions are at room temperature. The mixing is continued overnight (at least 15 hours) taking care to insulate the vessel so that heating from the magnetic stir plate does not occur. This can be accomplished by suspending the vessel above the stir plate leaving about an inch air space for insulation.

After the 15 hours mixing, the resulting suspension is divided equally into polypropylene centrifuge tubes (approximately 10 mL per tube) for a Sorvall SS-34 rotor [DuPont, Wilmington, Del., USA]. The suspension is centrifuged at 15,000 rpm (2700 ×g) for 60 minutes. The supernatant is decanted. The pellet is washed two times with 10 mM glycine buffer containing the desired overcoating protein [typically 1% protease free bovine serum albumin (BSA-pf) obtained from Miles Inc., Elkhart, Ind., USA]. To wash the pellet, a volume of wash solution equal to the original volume n the tube is added. The pellet is resuspended by vigorous vortexing and short-term sonication (10–15 seconds at a time). After the initial resuspension, the Ab-latex is allowed to stand at room temperature for one hour before recentrifuging. After the initial resuspension and centrifuging, subsequent resuspensions are centrifuged immediately once the pellet is completely dispersed. After the second wash, the pellets are resuspended in a volume equal to the initial reaction volume. The suspension is filtered through a 0.8μ filter and stored at 5° C.

The concentration is determined by measuring the absorbance at 546 nm of the original supernatant, the supernatant from the first and second washings, and a 100× dilution of the final sample. The sum of these absorbances is assumed to be 100% or equal to 0.5% latex. The absorbance of the final sample is divided by the sum of the absorbances used to calculate 100%. The absorbance of the 100× dilution of the final sample is multiplied by 100 to generate an absorbance for the final sample.

| Example: | |
|---|---|
| Sample | $A_{546}$ |
| Supernatant | 0.044 |
| First Wash | 0.034 |
| Second Wash | 0.021 |
| Final (100 × dil) | 0.051 × 100 = 5.1 |
| 100% (or 0.5% latex) = 5.10 + 0.044 + 0.034 + 0.021 = 5.199 | |
| Latex concentration of final sample = (5.1/5.199) × 0.5% = 0.49% | |

The concentrated Ab-Latex is diluted to 2.5% with 200 mM glycine buffer, pH 9 containing 0.05% BSA-pf. Mannitol at a 4% concentration may also be present in the buffer. Following dilution, the Ab-latex solution is sonicated briefly (5 to 10 sec.)

(3) Agglutinator reagent: Poly(aspartic acid) was prepared according to the procedure of Alpert, J. Chromatography 266:23(1983).

Aminoethanol (80 mmoles) and 4,9-dioxa-1,12-dodecanediamine (20 mmoles) were dissolved in dimethylformamide (DMF) under argon. The solution was treated with a solution of poly(aspartic acid) (10 mmoles) and DMF. The reaction was stirred at room temperature for 1 hour and then 70° C. for 2 hours. The mixture was then cooled and most of the liquid was removed by evaporation under reduced pressure. The oily residue was washed repeatedly with ether and then warm tetrahydrofuran. The product was solidified and recovered by filtration. The crude product was dissolved in water and the pH was adjusted to neutral. The solution was then purified with a BioRad P6-DG desalting gel column (BioRad Laboratories, Richmond, Calif., USA). Fractions containing the amino-functionalized polymer were pooled and lyophilized. The number of amino groups on the polymer was determined by Habeeb's TNBS assay [Anal. Biochem. 14:328–336(1966)] and found to be 22 per mg polymer.

Amino functionalized poly(aspartic acid) (10.7 mg) and SMCC (30 mg) were dissolved in DMF. The reaction was allowed to stir at room temperature for 2 hours. Ice water was added to the mixture and the activated polymer was separated from the mixture with a BioRad P6-DG gel column. The activated polymer was then allowed to react at room temperature for 3 minutes with the glycated peptide (20 mg):

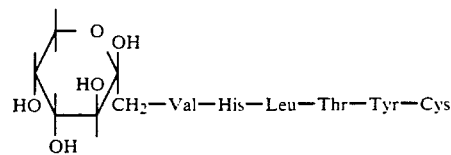

prepared according to the methods described in European patent publication 185,870. After the reaction, the product was again purified with a P6-DG gel column and lyophilized.

The number of maleimido groups on the activated polymers was determined by the PDS assay [Grassetti and Murray, Arch. Biochem. Biophys. 119:44–49(1967)] and found to be 0.46 μmole per mg polymer. The amount of Glc-peptide on the polymers was determined by UV/Vis absorption measurement using the molar extinction coefficient at 275 nm for tyrosine and found also to be 0.46 μmole per mg polymer.

A working solution of the agglutinator reagent is prepared from a 1.0 mg/mL water stock solution. A 50 μg/mL solution is prepared by diluting the stock with 20 mM citrate buffer, pH 4 containing 0.1% BSA-pf.

Procedure

Whole blood (10 μl) was mixed with 5 ml of the lysing/denaturing reagent and then allowed to stand at 37° C. At different time intervals, 0.5 ml of the treated blood sample was mixed with 10 μl of antibody-latex reagent (2.5%) and 10 μl of agglutinator reagent (50 μg/ml) and the immuno-reaction was monitored by measuring the absorbance at 540 nm. Complete denaturation was determined as the time required to reach the minimum absorbance and the results are shown in Table 3.

TABLE 3

| Cation | Conc. | Time Required For Complete Denaturation |
|---|---|---|
| Ammonium | 1.5M | ~4 min |
| Lithium | 0.5M | ~2.5 min |
| Lithium | 1.0M | ~1 min |
| Lithium | 1.5M | ~1 min |

C. Lysis of RBC with Hemoglobin Denaturation by Various Cationic Salts of Thiocyante Reagents The same reagents were used as in Part B above except that:
(a) The following series of lysing/denaturing reagent were used: 0.1, 0.5, 1.0, 1.25, or 2.5M thiocyanate solution (lithium, ammonium, potassium, or sodium) in 200 mM glycine containing 0.25% potassium ferricyanide at pH 9.0, and
(b) The working solution for the agglutinator reagent was prepared from a 1.0 mg/ml water stock solution by diluting to a 10 μg/ml solution with 20 mM citrate, pH 4, containing 0.1% BSA-pf.

Procedure

Figure 5:
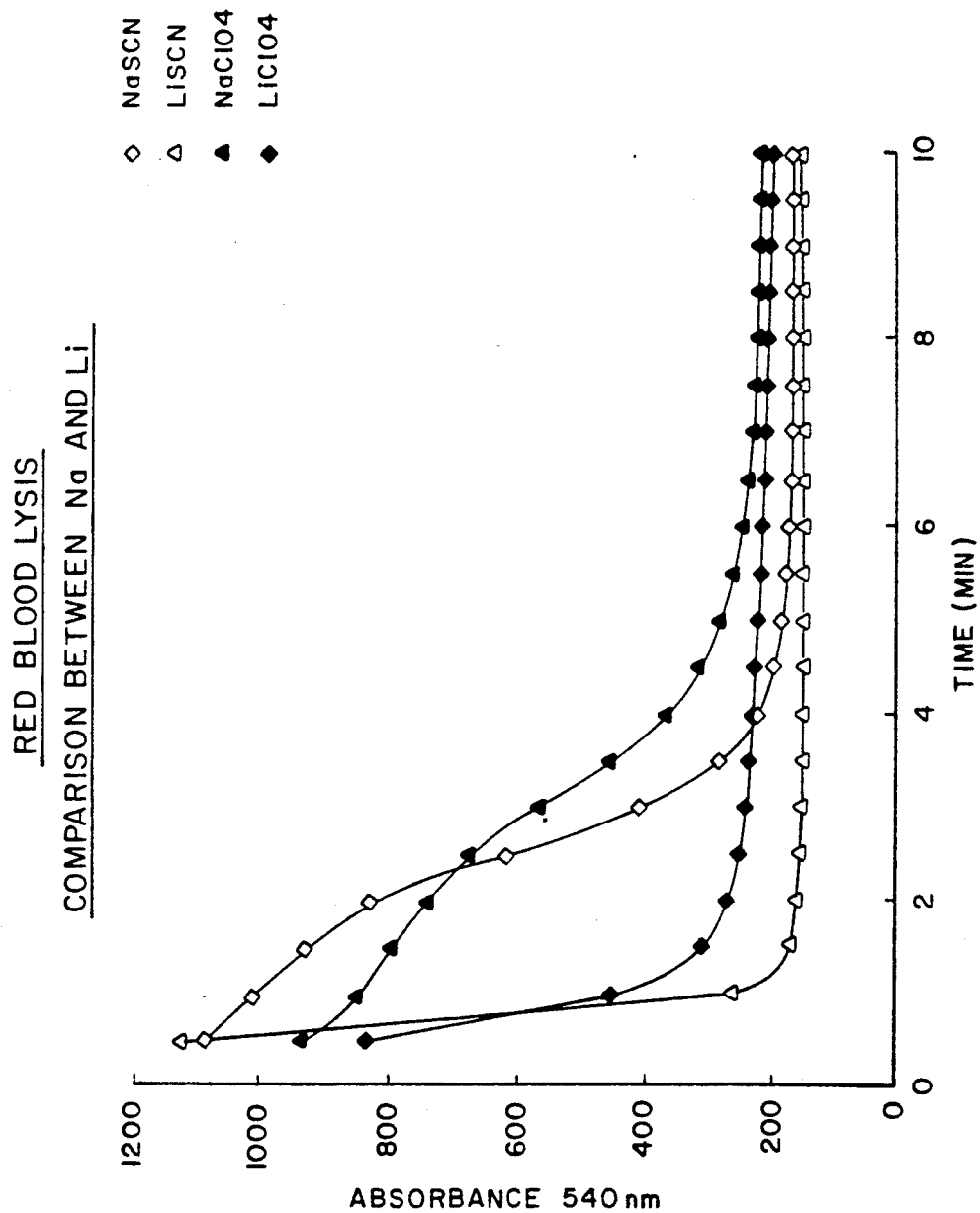
FIG. 5 is a graph showing the time courses for the lysis of RBC using the lithium and sodium salt forms of thiocyanate and perchlorate. The lithium salt outperformed the sodium salt in each case.

Whole blood was prediluted by mixing 1 part blood with 4 parts distilled water in order to completely lyse red blood cells and allow for more accurate delivery of blood. Diluted sample (5 μl) was mixed with 500 μl of lysing/denaturing reagent and was then allowed to incubate at 37° C. At appropriate time intervals, 0.5 ml of the treated blood sample was mixed with 10 μl of antibody-latex reagent (2.5%) and 10 μl of agglutinator reagent (10 μg/ml) and the immuno-reaction was monitored by measuring the absorbance at 540 nm. Complete denaturation was determined as the time required to reach the minimum absorbance and the results are shown in FIG. 5 and Table 4.

TABLE 4

| Cation | Thiocyanate Concentration, M | Time Required For Denaturation, Min. |
| --- | --- | --- |
| potassium | 0.1 | >10 |
|  | 0.5 | >10 |
|  | 1.0 | >10 |
|  | 1.25 | 9–10 |
|  | 2.5 | insufficient reactivity |
| sodium | 0.1 | >10 |
|  | 0.5 | >10 |
|  | 1.0 | >10 |
|  | 1.25 | 9–10 |
|  | 2.5 | insufficient reactivity |
| ammonium | 0.1 | >10 |
|  | 0.5 | >10 |
|  | 1.0 | 9–10 |
|  | 1.25 | 2–3 |
|  | 2.5 | insufficient reactivity |
| lithium | 0.1 | >10 |
|  | 0.5 | 8–9 |
|  | 1.0 | 3–4 |
|  | 1.25 | <1 |
|  | 2.5 | insufficient reactivity |

D. Lysis of RBC by Sodium and Lithium Salts of Various Anions

Figure 6:
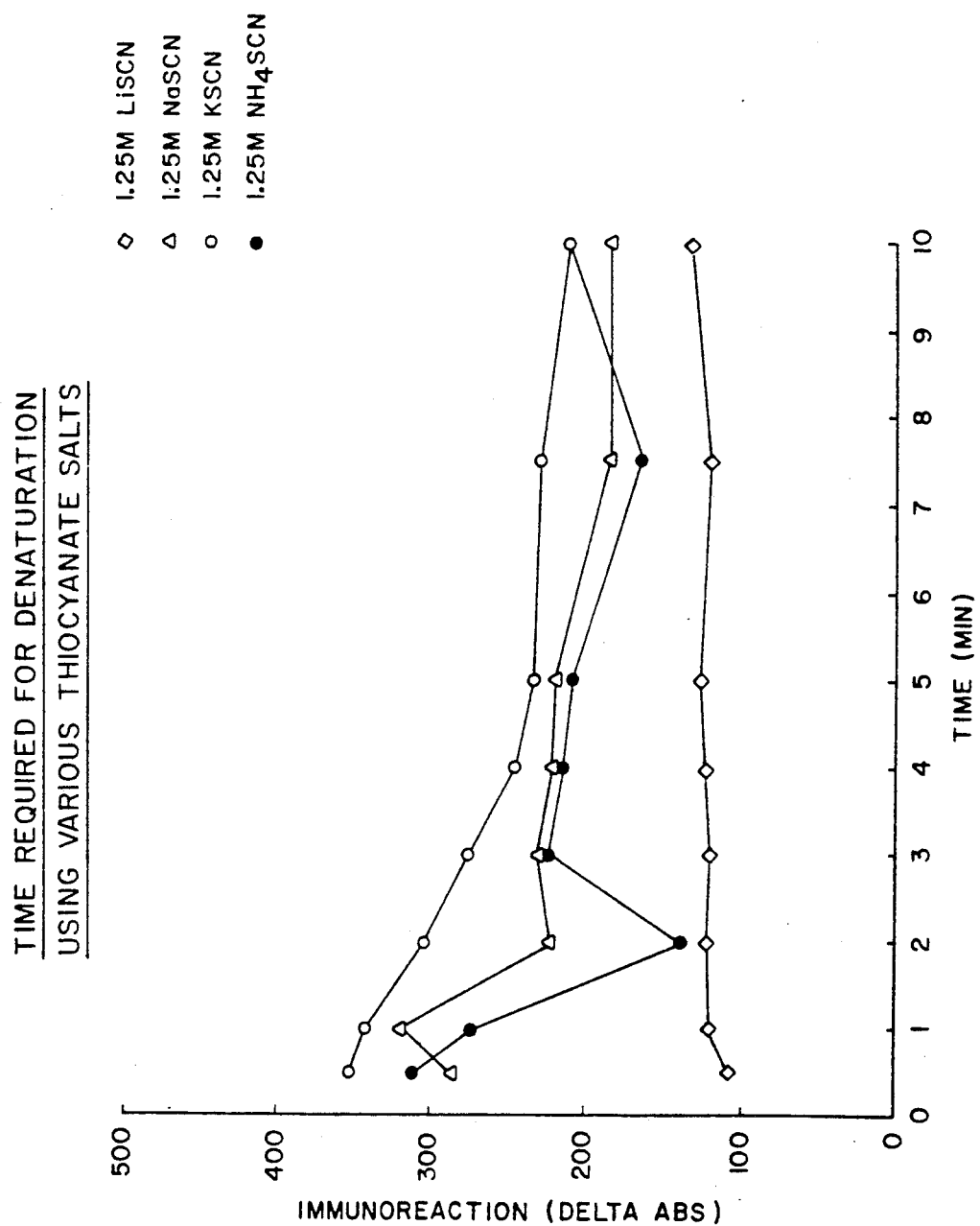
FIG. 6 is a graph showing the time course for the denaturation of hemoglobin using various thiocyanate salts. The data demonstrate that the lithium salt is the most efficient for hemoglobin denaturation.

Lysing solutions of 1.5M of the sodium and lithium salt forms of perchlorate, thiocyanate, chloride, hydroxide and acetate were prepared in 200 mM glycine, pH 9, and were equilibrated at 37° C. A 5 μl sample of fresh whole blood was pipetted into 2.5 ml of lysing solution and the absorbance at 540 nm was measured at 37° C. and recorded at 30 second intervals for 10 minutes. The rate of lysis was determined as the time required to reach an absorbance minimum. The results are shown in FIG. 6 and summarized in Table 5:

TABLE 5

| Salt Solution (1.5M) | Time Required for Complete Lysis |
| --- | --- |
| LiSCN | 1 min |
| NaSCN | 4 min |
| LiClO4 | 2 min |
| NaClO4 | 6 min |
| Li acetate | slow and incomplete |

No lysis was observed for the chloride or hydroxide salts up to 2.8M in the assay buffer system. In the case of acetate, some lysis was detected, however, the lysis was incomplete.

What is claimed is:

1. In an analytical method for determining a particular hemoglobin derivative in a blood sample, wherein (a) the blood sample is treated with a lysing/denaturing reagent comprising (i) a salt form of an anion that is capable of lysing erythrocytes and denaturing said hemoglobin derivative and (ii) an oxidant capable of converting hemoglobin to the met-hemoglobin form, and (b) the resulting mixture is assayed by immunoassay for the amount of the denatured form of said hemoglobin derivative present therein, the improvement which comprises employing a lithium salt form of said anion that is capable of lysing erythrocytes and denaturing said hemoglobin derivative, said lithium salt being present in said resulting mixture at a concentration of between about 1.0 and about 1.5 molar, whereby the erythrocyte lysis and denaturation of said hemoglobin derivative is accomplished in less than about one minute without interfering significantly with the immunoassay step.

2. The method of claim 1 wherein said lithium salt form of said anion is lithium thiocyanate.

3. The method is claim 2 wherein said lithium thiocyanate is added in an amount to give a concentration of about 1.25 molar.

4. The method of claim 1 performed at between about 20° C. and about 37° C.

5. The method of claim 1 wherein the oxidant is a ferricyanide salt.

6. The method of claim 1 wherein the particular hemoglobin derivative to be determined is hemoglobin A1c.

* * * * *